US009970067B2

(12) United States Patent
Rose et al.

(10) Patent No.: US 9,970,067 B2
(45) Date of Patent: May 15, 2018

(54) PRIMERS AND PROBES FOR DETECTION AND DISCRIMINATION OF EBOLA VIRUS (71) Applicant: Integrated DNA Technologies, Inc., Coralville, IA (US)

(72) Inventors: Scott Rose, Coralville, IA (US); Kristin Beltz, Cedar Rapids, IA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 0 days. days.

(21) Appl. No.: 14/943,894

(22) Filed: Nov. 17, 2015

(65) Prior Publication Data

US 2016/0145698 A1    May 26, 2016

Related U.S. Application Data (60) Provisional application No. 62/082,717, filed on Nov. 21, 2014.

(51) Int. Cl.
*C12Q 1/70* (2006.01)
*C07K 14/005* (2006.01)
*C12Q 1/68* (2018.01)

(52) U.S. Cl.
CPC ........... *C12Q 1/701* (2013.01); *C07K 14/005* (2013.01); *C12Q 1/6827* (2013.01); *C12Q 1/6883* (2013.01)

(58) Field of Classification Search
None
See application file for complete search history.

(56) References Cited

U.S. PATENT DOCUMENTS

2007/0082011 A1* 4/2007 Lehrer .................. A61K 39/12
424/204.1

OTHER PUBLICATIONS

Sanchez et al., Detection and Molecular Characterization of Ebola Viruses Causing Disease in Human and Nonhuman Primates, 1999, Journal of Infectious Diseases, vol. 179, Supplemental 1, S164-S169.*

Towner et al., High-Throughput Molecular Detection of Hemorrhagic Fever Virus Threats with Applications for Outbreak Settings, 2007, Journal of Infectious Diseases, vol. 196, S205-212.*

* cited by examiner

*Primary Examiner* — Benjamin P Blumel
(74) *Attorney, Agent, or Firm* — John A. Petravich (57) ABSTRACT

This invention relates to primers and probes for detecting Ebola virus and one or more subtypes of Ebola virus as well as kits including the probes and primers and methods of using the probes and primers.

6 Claims, 4 Drawing Sheets

| Lane | Sample | Conc (ng/ul) |
|---|---|---|
| 1 | IVT #1 (frag1 IVT-10nM no biotin DNA) | 1300.7 |
| 2 | IVT #2 (frag2 IVT-10nM no biotin DNA) | 1102.7 |
| 3 | IVT #3 (frag1 IVT-25nM no biotin DNA) | 1379.3 |
| 4 | IVT #4 (frag2 IVT-25nM no biotin DNA) | 1356.0 |
| 5 | IVT #5 (frag1 IVT-10nM +biotin DNA) | 1260.0 |
| 6 | IVT #6 (frag2 IVT-10nM +biotin DNA) | 1100.0 |
| 7 | IVT #7 (frag1 IVT-25nM +biotin DNA) | 1232.0 |
| 8 | IVT #8 (frag2 IVT-25nM +biotin DNA) | 1108.0 |
| 9 | IVT control | |

FIG. 1A

| Lane | Sample | Conc (ng/ul) |
|---|---|---|
| 1 | Control IVT | |
| 2 | Control IVT | |
| 3 | IVT RNase P - RPPH1 (347 nt transcript) | 679 |
| 4 | Hela total RNA | 250 |
| 5 | Hela total RNA | 1370 |

SEQUENCE LISTING

```
<160> NUMBER OF SEQ ID NOS: 37

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
catcatgcgt accaaggaga ttac                                              24

<210> SEQ ID NO 2
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 2
ccagcagtat ctagtgggag aa                                                22

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonulceotide

<400> SEQUENCE: 3
cgcaggagta aatgttggag aa                                                22

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
ggacagggac ggaacttcta a                                                 21

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
tgaagcgcct tgaggaattg                                                   20

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
gaaagtggcg cagtcaagta t                                                 21

<210> SEQ ID NO 7
<211> LENGTH: 22
<212> TYPE: DNA
<213> ORGANISM: Artificial Sequence
```

```
<220> FEATURE:
<223> OTHER INFORMATION: Synthetic oligonucleotide

<400> SEQUENCE: 7
cactcacgga caatgacaga ag                                        22

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 8
tgatgaagga tgagcctgta gtt                                       23

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 9
catgcagagc aaggactgat ac                                        22

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 10
catgagtgca ccagatgact tg                                        22

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
cgcttcactc catcacactt c                                         21

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
gacttgcaaa ggagaggaac tg                                        22

<210> SEQ ID NO 13
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 13
gttcacgaga ctccgcatat tg                                        22
```

<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 14
gttcatcttg cgggagttct tt                                              22

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
agaggaactg accggcatta                                                 20

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 16
catggcagca agtgttctct ta                                              22

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
atctgactct aagggcggaa g                                               21

<210> SEQ ID NO 18
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 18
tcagtgagcc atggtggata tt                                              22

<210> SEQ ID NO 19
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 19
catgtgcatc ccttggtgta tt                                              22

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 20
tgtctgtctg ccctctgtat g                                              21

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 21
tcaagtattt ggaagggcac gggt                                           24

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 22
accggcatta gcttcagtcg tctc                                           24

<210> SEQ ID NO 23
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 23
actgaggctg agaagcaact ccaa                                           24

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
accggctccc gtatacagag atca                                           24

<210> SEQ ID NO 25
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 25
atgccggaag aggagacgac tgaa                                           24

<210> SEQ ID NO 26
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 26
atggagtgaa gcgccttgag gaat                                           24

<210> SEQ ID NO 27

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 27
ccaatcaacg aagaggcaga ccca                                          24

<210> SEQ ID NO 28
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 28
agtacacgta tccggactcc cttgaa                                        26

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 29
acagcttggc aatcagtagg acaca                                         25

<210> SEQ ID NO 30
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 30
acaccaagcc agtgcctaac agat                                          24

<210> SEQ ID NO 31
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 31
gcggagggaa gctcatcag                                                19

<210> SEQ ID NO 32
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 32
ccctagtctc agaccttccc aag                                           23

<210> SEQ ID NO 33
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 33
```
cacgagctga gtgcgtcctg tcac    24

<210> SEQ ID NO 34
<211> LENGTH: 893
<212> TYPE: DNA
<213> ORGANISM: Artificial Sequence
<220> FEATURE:
<223> OTHER INFORMATION: Synthetic oligonucleotide

<400> SEQUENCE: 34
gaattctaat acgactcact atagggagag ttcacgagac tccgcatatt gttggagttg    60
cttctcagcc tcagtggctg cctctctgag ctgttgatac tgttctccaa catttactcc    120
tgcgagggtg ctcccgtggg ctgtggcgac tccgagtgca attgccgaca gttgagggaa    180
aagaccatgc tcaagattat ttactccaga aaggttcaaa agtcgggcga aggagcata     240
ctctccatgc ttggccaggg agctgagtgc agccttgaag gagttcacct cattttttac    300
cttggcggtc cttgcaagag gatggagacg aactcctcgt tctgtctttt gtaggatatg    360
atcaagtact gttttgacaa tcaatagacc tgaaaaacga gcttgagcca ctgaatttga    420
aatcacagca tcgttggcat catgtccggc aaccatgtgc atcccttggt gtattagaag    480
aaatttgatc aaaaaatttg ttcgcatcaa acggaaaatc accatcatgt gtcctactga    540
ttgccaagct gttggatatt gtatcagtcc ttgctctgca tgtacttgaa tttgcctttg    600
aaccttctca aggcaagcct tttctcctac taccaatttc ggaaggaata gacttgcaaa    660
ggagaggaac tgaccggcat tagcttcagt cgtctcctct tccggcatgg cagcaagtgt    720
tctcttaatg tttctcccac tagatactgc tggcagcaat tcctcaaggc gcttcactcc    780
atcacacttc ttgacttcaa aacggaaccc gtgcccttcc aaatacttga ctgcgccact    840
ttccaagaaa agtttgtaat ctccttggta cgcatgatga agacagcggc cgc           893

<210> SEQ ID NO 35
<211> LENGTH: 766
<212> TYPE: DNA
<213> ORGANISM: Artificial Sequence
<220> FEATURE:
<223> OTHER INFORMATION: Synthetic oligonucleotide

<400> SEQUENCE: 35
gaattctaat acgactcact atagggagat tctcatcatt catggcctct ttttcagtga    60
gccatggtgg atattcctct tcaagggagt ccggatacgt gtactcttta ccatcactgg    120
tactgaaaac tacaggctca tccttcatca tatgataata caaaacggca tcaaatggcc    180
cctgtgatct tagaatgtgg cgatacatct cctcaaaaga atgttctggc tgggtgttgt    240
cactgtcttg gttcctggcc tcttgaatgt ggtcctgatc ttgttgttca tcttgcggga    300
gttcttcctt ttcggagtga tctctgtata cgggagccgg tggggcgaca gtgggtgtgc    360
ggttagaagt tccgtccctg tcctgttctt catcatctga ctctaagggc ggaaggctag    420
acgtctcgtc gtcggcatcg tccagtgggt ctgcctcttc gttgattggg gtcagcatgc    480
gagggctggt tgagccggag ggttcgtttc ttctgtcatt gtccgtgagt ggagcactgg    540
catggtggat tgttctgcga gggcctgtga cgttttgagt tggcgtggat tgtgtctgtc    600
tgccctctgt atgctggccc ttttgactgt ttttctgttg tccacccttg gtcgatctgt    660
taggcactgg cttggtgtcc tcgtcgtcct cgtctagatc gaataggacc aagtcatctg    720
gtgcactcat gccgttttcc gagtaacttt ggtattcggc ggccgc                   766

<210> SEQ ID NO 36
<211> LENGTH: 364
<212> TYPE: DNA
<213> ORGANISM: Artificial Sequence
<220> FEATURE:
<223> OTHER INFORMATION: Synthetic oligonucleotide

<400> SEQUENCE: 36

```
taatacgact cactataggg agaatagggc ggagggaagc tcatcagtgg ggccacgagc        60
tgagtgcgtc ctgtcactcc actcccatgt cccttgggaa ggtctgagac tagggccaga      120
ggcggcccta acagggctct ccctgagctt cggggaggtg agttcccaga gaacggggct      180
ccgcgcgagg tcagactggg caggagatgc cgtggacccc gcccttcggg gaggggcccg      240
gcggatgcct cctttgccgg agcttggaac agactcacgg ccagcgaagt gagttcaatg      300
gctgaggtga ggtaccccgc aggggacctc ataacccaat tcagactact ctcctccgcc      360
catt                                                                   364
```

<210> SEQ ID NO 37
<211> LENGTH: 2221
<212> TYPE: DNA
<213> ORGANISM: Artificial Sequence
<220> FEATURE:
<223> OTHER INFORMATION: Synthetic oligonucleotide

<400> SEQUENCE: 37

```
atggattctc gtcctcagaa agtctggatg acgccgagtc tcactgaatc tgacatggat        60
taccacaaga tcttgacagc aggtctgtcc gttcaacagg ggattgttcg gcaaagagtc      120
atcccagtgt atcaagtaaa caatcttgag gaaatttgcc aacttatcat acaggccttt      180
gaagctggtt tgattttca agagagtgcg gacagtttcc ttctcatgct ttgtcttcat       240
catgcgtacc aaggagatta caaacttttc ttggaaagtg gcgcagtcaa gtatttggaa      300
gggcacgggt ccgttttga gtcaagaag tgtgatggag tgaagcgcct tgaggaattg         360
ctgccagcag tatctagtgg gagaaacatt aagagaacac ttgctgccat gccggaagag      420
gagacgactg aagctaatgc cggtcagttc ctctcctttg caagtctatt ccttccgaaa      480
ttggtagtag agaaaaggc ttgccttgag aaggttcaaa ggcaaattca agtacatgca        540
gagcaaggac tgatacaata tccaacagct tggcaatcag taggacacat gatggtgatt      600
ttccgtttga tgcgaacaaa ttttttgatc aaatttcttc taatacacca agggatgcac      660
atggttgccg acatgatgc caacgatgct gtgatttcaa attcagtggc tcaagctcgt       720
ttttcaggtc tattgattgt caaaacagta cttgatcata tcctacaaaa gacagaacga      780
ggagttcgtc tccatcctct tgcaaggacc gccaaggtaa aaaatgaggt gaactccttc      840
aaggctgcac tcagctccct ggccaagcat ggagagtatg ctcctttcgc ccgacttttg      900
aacctttctg gagtaaataa tcttgagcat ggtcttttcc ctcaactgtc ggcaattgca      960
ctcggagtcg ccacagccca cgggagcacc ctcgcaggaa taaatgttgg agaacagtat     1020
caacagctca gagaggcagc cactgaggct gagaagcaac tccaacaata tgcggagtct     1080
cgtgaacttg accatcttgg acttgatgat caggaaaaga aaattcttat gaacttccat     1140
cagaaaaaga acgaaatcag cttccagcaa acaaacgcga tggtaactct aagaaaagag     1200
cgcctggcca agctgacaga agctatcact gctgcatcac tgcccaaaac aagtggacat     1260
tacgatgatg atgacgacat tccctttcca ggacccatca atgatgacga caatcctggc     1320
catcaagatg atgatccgac tgactcacag gatacgacca ttcccgatgt ggtagttgac     1380
```

-continued

```
cccgatgatg gaggctacgg cgaataccaa agttactcgg aaaacggcat gagtgcacca    1440
gatgacttgg tcctattcga tctagacgag gacgacgagg acaccaagcc agtgcctaac    1500
agatcgacca agggtggaca acagaaaaac agtcaaaagg gccagcatac agagggcaga    1560
cagacacaat ccacgccaac tcaaaacgtc acaggccctc gcagaacaat ccaccatgcc    1620
agtgctccac tcacggacaa tgacagaaga aacgaaccct ccggctcaac cagccctcgc    1680
atgctgaccc caatcaacga agaggcagac ccactggacg atgccgacga cgagacgtct    1740
agccttccgc ccttagagtc agatgatgaa gaacaggaca gggacggaac ttctaaccgc    1800
acacccactg tcgccccacc ggctcccgta tacagagatc actccgaaaa gaaagaactc    1860
ccgcaagatg aacaacaaga tcaggaccac attcaagagg ccaggaacca agacagtgac    1920
aacacccagc cagaacattc ttttgaggag atgtatcgcc acattctaag atcacagggg    1980
ccatttgatg ccgttttgta ttatcatatg atgaaggatg agcctgtagt tttcagtacc    2040
agtgatggta aagagtacac gtatccggac tcccttgaag aggaatatcc accatggctc    2100
actgaaaaag aggccatgaa tgatgagaat agatttgtta cactggatgg tcaacaattt    2160
tattggccag taatgaatca caggaataaa ttcatggcaa tcctgcaaca tcatcagtga    2220
a                                                                    2221
```

PRIMERS AND PROBES FOR DETECTION AND DISCRIMINATION OF EBOLA VIRUS

CROSS-REFERENCE TO RELATED APPLICATIONS

This patent application claims priority to U.S. Provisional Patent Application No. 62/082,717 filed Nov. 21, 2014, the content of which is incorporated herein by reference in its entirety.

SEQUENCE LISTING

The sequence listing is filed with the application in electronic format only and is incorporated by reference herein. The sequence listing text file "Primers and Probes for Detection and Discrimination of Ebola Virus" was created on Nov. 17, 2015 and is 13 kb in size.

FIELD OF THE INVENTION

This invention relates to primers and probes for detecting Ebola virus and one or more subtypes of Ebola virus as well as kits including the probes and primers and methods of using the probes and primers.

BACKGROUND OF THE INVENTION

Ebola virus is a single stranded negative sense RNA virus that belongs to the family Filoviridae and is a causative agent of viral hemorrhaghic fever (VHF). VHF viruses belong to the Filoviridae (which includes Marburg virus and Ebola virus), Arenaviridae (Lassa virus, Junin, Machupo, Sabia, and Guanarito viruses), Bunyaviridae (Crimean-Congo hemorrhagic fever virus, Rift Valley fever virus and Hanta virus), and Flaviviridae families.

There are five known species of Ebola virus: 1) Zaire Ebola virus; 2) Sudan Ebola virus; 3) Reston Ebola virus; 4) Tai: Forest virus, formerly the Cote d'Ivoire Ebola virus; and 5) Bundibugyo. Zaire Ebola virus is often considered the most virulent in humans. Although there are a number of species of Ebola virus the genomic structure of the filoviruses are very similar. The genome of the Ebola virus is approximately 19 kb in length and contains seven genes arranged sequentially in order from nucleoprotein (NP); viral protein 35(VP 35); VP40; glycoprotein (GP); VP 30; VP 24; and RNA polymerase (L).

Infection by VHF viruses results in rapid disease progression and high mortality rates. Infection by VHF viruses are associated with a wide spectrum of clinical manifestations, such as hemorrhage, diarrhea, myalgia, cough, headache, and pneumonia. Hemorrhage is the characteristic clinical manifestation of all VHF, although non-hemorrhagic infections are common. In the absence of bleeding or other organ manifestation it is often difficult to properly diagnose a VHF, and it can often be mistaken for other etiologic agents.

There are a number of currently available techniques to diagnose VHF and Ebola infections. These diagnostic assays include viral culture, immunohistochemistry, transmission electron microscopy, antigen ELISAs, and antibody ELISAs. However these techniques have a number of disadvantages which do not allow cheap, rapid, accurate and specific detection of Ebola viruses. For example viral culture is sensitive but highly specialized biological safety level 4 labs are required. Additionally viral cultures propagate the highly infectious virus. Transmission electron microscopy, although rapid, requires highly specialized lab equipment and trained personnel which precludes its use in the field for rapid detection. Antibody ELISAs are often unreliable because symptomatic patients fail to mount a detectable immune response prior to death. Antigen ELISAs provide rapid and accurate detection in the acute stages of infection but require the handling of highly infectious samples.

Reverse Transcriptase PCR is more sensitive than antigen ELISAs and has the added benefit of rendering the sample noninfectious prior to testing. RT-PCR can be easily deployed in the field to provide rapid and accurate testing. However, due to the conserved genomic sequence of Ebola and related VHF causative agents, prior RT-PCR assays often result in false positive results. Additionally prior RT-PCR assays are unable to reliably positively identify and detect all known subtypes of the Ebola virus.

The main route of transmission of VHF causative agents is contact with contaminated bodily fluids, such as direct contact with infected tissue or samples, close contact with infected patients, improper use of personal protective equipment or accidental exposure to contaminated laboratory equipment, such as, for example, needles. Because of the mode of transmission, high mortality rates, and need to follow and institute proper contamination controls and public health measures during an outbreak it is imperative to establish an early and accurate diagnosis. With a rapid and accurate diagnosis public health officials can institute appropriate case management procedures such as isolation measures or tracking of contact persons.

There is a present need for a test that provides sensitive, specific detection of VHF and Ebola viruses in a relatively short time and without the need of specialized laboratories, specialized training, or specialized equipment. Additionally there is a need for a rapid diagnosis that reduces autoinfection by laboratory technicians. Furthermore there is a need for a diagnostic assay that can be completed in sufficient time to permit effective treatment of the infected person and provide appropriate safeguards, such as isolation and contact surveillance.

BRIEF SUMMARY OF THE INVENTION

The invention relates to a method of detecting and identifying the Ebola virus in a sample, such as a biological sample obtained from a subject. The disclosed methods can be used for diagnosing an Ebola infection in a subject suspected of having Ebola by analyzing a biological specimen from the subject. Alternatively, the method can be used to quickly identify particular types and subtypes of Filoviridae particularly Ebola virus and those viruses that may be involved in pandemics. In addition, panels of probes are provided that permit the rapid evaluation of a subject with an apparent viral illness by quickly determining whether the illness is caused by a virulent virus such as the Ebola Zaire virus. This rapid evaluation involves ruling out the presence of other etiological agents such as *Shigella* dysentery and malaria, ruling in the presence of Ebola virus, or a combination of both.

In some embodiment, the method involves hybridizing an Ebola virus RNA to an Ebola specific probe between 15 and 30 nucleotides in length, and detecting hybridization between Ebola RNA and the probe. In some embodiments, the probe is detectably labeled. In some embodiments, the probe is capable of hybridizing under conditions of very high stringency to an Ebola nucleic acid sequence set forth as SEQ ID NO: 34, SEQ ID NO:35, or SEQ ID NO: 37. In specific embodiments, the probe includes a nucleic acid sequence that is at least 95% identical to a nucleic acid sequence set forth as SEQ ID:21, SEQ ID NO:22, SEQ ID NO: 23, SEQ ID NO:24, SEQ ID NO:25, SEQ ID NO:26, SEQ ID NO: 27, SEQ ID NO:28, SEQ ID NO:29, or SEQ ID:30.

In some embodiments, the methods disclosed herein include amplifying the Ebola nucleic acids with at least one primer specific for an Ebola nucleic acid. In some embodiments, the primer specific for an Ebola nucleic acids is 15 to 40 nucleotides in length and is capable of hybridizing under very high stringency conditions to an Ebola virus nucleic acid sequence set forth as SEQ ID NO: 34, SEQ ID NO:25, or SEQ ID NO:37. In some embodiments, the primer specific for an Ebola virus nucleic acid is 15-40 nucleotides in length and includes a nucleic acid sequence at least 95% identical to the nucleotide sequence set forth as SEQ ID NO:01, SEQ ID NO:02, SEQ ID NO:03, SEQ ID NO:04, SEQ ID NO:05, SEQ ID NO:06, SEQ ID NO:07, SEQ ID NO:08, SEQ ID NO:09, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, or SEQ ID NO:20.

Additional methods for detecting, typing, and/or subtyping an Ebola virus in a sample include hybridizing nucleic acids in the sample to at least one Ebola virus type and/or subtype specific probe.

This disclosure also relates to probes capable of hybridizing to and discriminating between Ebola virus nucleic acids form specific types and/or subtypes. In some embodiments, these probes are between 15 and 30 nucleotides in length and capable of hybridizing under very high stringency conditions to an Ebola virus nucleic acid sequence set forth as SEQ ID NO: 34, SEQ ID NO:35 or SEQ ID NO:37.

In a further embodiment, the disclosure also relates to probes capable of hybridizing to and discriminating between Ebola virus nucleic acids form specific types and/or subtypes. In some embodiments, these probes are 24 nucleotides in length and capable of hybridizing under very high stringency conditions to an Ebola virus nucleic acid sequence set forth as SEQ ID NO: 34, SEQ ID NO:35 or SEQ ID NO:37.

In a further embodiment, the disclosure also relates to probes capable of hybridizing to and discriminating between Ebola virus nucleic acids form specific types and/or subtypes. In some embodiments, these probes are 15-23 nucleotides in length, containing one or more modified bases or modifications capable of improving stability, wherein the probe capable of hybridizing under very high stringency conditions to an Ebola virus nucleic acid sequence set forth as SEQ ID NO: 34, SEQ ID NO:35 or SEQ ID NO:37. In a further embodiment, the modified bases or modifications are comprised of locked nucleic acids (LNAs), bicyclic nucleic acids (BNAs), minor groove binder (MGB) and ZEN.

The foregoing and other objects, features, and advantages of the invention will become more apparent form the following detailed description, which proceeds with reference to the accompanying figures.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs, such as LNA, BNA, 2'-O-alkyl, 2'-fluoro, etc. If present, modifications to the nucleotide structure may be imparted before or after assembly of the polymer. The sequence of nucleotides may be interrupted by non-nucleotide components such as C3 spacers or stability enhancers such as intercalators (see U.S. Pat. No. 4,835,263) or those described in U.S. App. No. 2011/0236898. A polynucleotide may be further modified after polymerization, such as by conjugation with a labeling component.

The term "base" as used herein includes purines, pyrimidines and non-natural bases and modifications well-known in the art. Purines include adenine, guanine and xanthine and modified purines such as 8-oxo-$N^6$-methyladenine and 7-deazaxanthine. Pyrimidines include thymine, uracil and cytosine and their analogs such as 5-methylcytosine and 4,4-ethanocytosine. Non-natural bases include 5-fluorouracil, 5-bromouracil, 5-chlorouracil, 5-iodouracil, hypoxanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, nitroindole, and 2,6-diaminopurine.

The term "base" is sometimes used interchangeably with "monomer", and in this context it refers to a single nucleic acid or oligomer unit in a nucleic acid chain.

The term "probe" as used herein refers to nucleic acid oligonucleotides that produce a detectable response upon interaction with a target. The probes include at least one detectable moiety, a pair of moieties that form an energy transfer pair detectable upon some change of state of the probe in response to its interaction with a binding partner, or more than two moieties such as a fluorophore and more than one quencher.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (e.g., a DNA polymerase or reverse transcriptase) in an appropriate buffer and at a suitable temperature. A primer is preferably a single-stranded DNA. The appropriate length of a primer depends on the intended use of the primer but typically ranges from 6 to 50 nucleotides, preferably from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein. Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product. The region of the primer which is sufficiently complementary to the template to hybridize is referred to herein as the hybridizing region.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

Some of the oligonucleotides disclosed herein include a fluorophore, which may include, but is not limited to, 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX); 1-dimethylaminonaphthyl-5-sulfonate, 1-anilino-8-naphthalene sulfonate, 2-p-toluidinyl-6-naphthalene sulfonate, 5-(2'-aminoethyl)aminonaphthalene-1-sulfonic acid (EDANS), a coumarin dye, an acridine dye, indodicarbocyanine 3 (Cy3), indodicarbocyanine 5 (Cy5), indodicarbocyanine 5.5 (Cy5.5), 3-1-carboxy-pentyl)-3'-ethyl-5,5'-dimethyloxacarbocyanine (CyA); 1H,5H,11H,15H-Xantheno[2, 3,4-ij:5,6,7-i'j']diquinolizin-18-ium, 9-[2(or 4)-[[[6-[2,5-dioxo-1-pyrrolidinyl)oxy]-6-oxohexyl]amino]sulfonyl]-4 (or 2)-sulfophenyl]-2,3,6,7,12,13,16,17-octahydro-inner salt (TR or Texas Red), a BODIPY™ dye, benzoxaazole, stilbene and pyrene. In some embodiments, the fluorophore may be attached to the 5' end, such as to the phosphate at the 5' end of the oligonucleotide.

Some of the oligonucleotides disclosed herein may include more than one quencher, such as a first internal quencher and a second quencher. The second quencher may be placed internally or placed at a terminal end of the oligonucleotide. The second quencher may include, but is not limited to, an azo quencher and an anthraquinone quencher, although any quencher may be used. Examples of azo quenchers include, but are not limited to, dabcyl, Eclipse® quencher, BHQ1, BHQ2 and BHQ3, and Iowa Black® FQ. Examples of anthraquinone quenchers include, but are not limited to, the anthraquinone quencher shown above, Iowa Black® RQ-n1 or Iowa Black® RQ-n2 (see, e.g., Laikhter et al., U.S. Patent App. 2004/0110308). Attachment of multiple quenchers to a probe not only can enhance quenching efficiency but also can provide effective quenching of various fluorophores that fluoresce over a broad spectral range.

The compositions of the present disclosure may be used in various assays for detecting target nucleic acids within a sample. Such methods may include contacting the sample with an oligonucleotide adapted to hybridize to the target nucleic acid, where the oligonucleotide includes an internal quencher and a fluorophore, and where the fluorescence of the fluorophore is reduced by fluorescence resonance energy transfer to the quencher and/or by ground state quenching by the quencher when the oligonucleotide is not hybridized to the second oligonucleotide, and detecting an increase in fluorescence indicating the presence of the second oligonucleotide in the sample. In some assays, such as the 5'-nuclease hydrolysis assay, the increase in fluorescence arises from cleavage of the labeled oligonucleotide. In some assays, the oligonucleotide forms a random-coil conformation when the oligonucleotide is unhybridized, such that the fluorescence of the fluorophore is reduced. In some assays, the oligonucleotide comprises a self-complimentary sequence, and the quencher and fluorophore are attached to the oligonucleotide such that the fluorescence of the fluorophore is quenched by the quencher when the nucleic acid polymer undergoes intramolecular base pairing. These assays have many applications, including, but not limited to, monitoring PCR reactions, where synthesis of the PCR product results in an increase in fluorescence.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two step cycles have a high temperature denaturation step followed by a hybridization/ elongation (or ligation) step. Three step cycles comprise a denaturation step followed by a hybridization step followed by a separate elongation or ligation step.

Investigators herein disclose composition of matter and methods used to detect and/or quantify Ebola virus.

The Ebola virus is a member of the family Filoviridae that includes at least five Ebola subtypes and the Marburg virus. Currently there are at least 5 recognized Ebola subtypes which include: 1) Zaire Ebola virus; 2) Sudan Ebola virus; 3) Reston Ebola virus; 4) Tai: Forest virus, formerly the Cote d'Ivoire Ebola virus; and 5) Bundibugyo. Further genotypic and phenotypic variances in the Ebola virus may interchangeably be called strains, subtypes or variants.

The Ebola virus has a single stranded negative sense (or antisense) RNA genome. The genome of the Ebola virus is about 19 kb in length and contains seven genes arranged in sequential order. The 7 genes in order are nucleoprotein (NP), viral protein 35 (VP 35), viral protein 40 (VP40), glycoprotein (GP), viral protein 30 (VP 30), viral protein 24 (VP 24), and RNA polymerase (L).

Disclosed herein are methods for the detection of Ebola Zaire virus. The methods have been developed in one embodiment with a unique set of nucleic acid probes and/or primers that are surprisingly effective at detecting and discriminating between Ebola Zaire and other VHF viruses. This ability to rapidly screen and identify a virus from among a diverse group of VHF viruses is a significant public health advantage.

Polymerase chain reaction (PCR) is a particular method of amplifying DNA, generally involving the mixing of a nucleic sample, two or more primers, a DNA polymerase, which may be a thermostable DNA polymerase such as Taq or Pfu, and deoxyribose nucleoside triphosphates (dNTP's) In general, the reaction mixture is subjected to temperature cycles comprising a denaturation stage, (typically 80-100° C.) an annealing stage with a temperature based upon the melting temperature (Tm) of the primers and the degeneracy of the primers, and an extension stage (for example 40-75° C.) In real-time PCR analysis, additional reagents, methods, optical detection systems, and devices are used that allow a measurement of the magnitude of fluorescence in proportion to concentration of amplified DNA. In such analyses, incorporation of fluorescent dye into the amplified strands may be detected or labeled probes that bind to a specific sequence during the annealing phase release their fluorescent tags during the extension phase. Either of these will allow a quantification of the amount of specific DNA present in the initial sample. RNA may be detected by PCR analysis by creating a DNA template from RNA through a reverse transcriptase enzyme. In some aspects of the invention, the marker may be detected by quantitative PCR analysis, which may be performed using a kit containing components that facilitate genotyping analysis. Genotyping analysis may be performed using a probe that is capable of hybridizing to a nucleic acid sequence of interest.

The underlying basis for the qPCR assay is that Taq polymerase possesses both endonuclease and polymerase activities. Once the cDNA is formed by the action of Reverse Transcriptase, oligonucleotide-specific primers are used for the amplification aspect of PCR. Hybridizing "between" the primers on the cDNA, the dual-labeled probe contains a reporter fluorophore, which can be, for example, FAM at the 5' end of the oligonucleotide, and a quencher dye, which can be, for example, Iowa Black IQ (Integrated DNA Technologies, Inc.), Zen (Integrated DNA Technologies, Inc. or Tamra, at the 3' end of the probe. The probe itself is not fluorescent, due to intramolecular fluorescence quenching. Thus, when the probe is intact, the proximity of the reporter fluorophore to the quencher dye results in suppression of the reporter fluorescence, primarily by Forster-type energy transfer. As the PCR proceeds, amplification of the target cDNA occurs and the DNA polymerase, during extension of the primer sequences, effects the 5' cleavage of the probe reporter, resulting in a reversal of quenching of fluorescence of the reporter and, hence, in a measurable fluorescent signal of cDNA production. The amplified material is discarded without opening the test tubes. Thus, the contamination of the samples by amplified DNA can be completely avoided.

EXAMPLES

Elements and acts in the examples are intended to illustrate the invention for the sake of simplicity and have not necessarily been rendered according to any particular sequence or embodiment. The example is also intended to establish possession of the invention by the Inventors.

Example 1

Design of qPCR Assays to Detect Zaire Ebola Viral RNA

Zaire Ebola sequences derived from isolates of infected patients in Sierra Leone that were deposited at NCBI were aligned using DNASTAR Lazergene 10 MegAlign program. The consensus sequence for the coding region of NP gene (SEQ ID No. 37), was used to design 5' exonuclease assays using PrimerQuest software (Integrated DNA Technologies). Primers and probes were subjected to BLAST analysis to verify their inability to cross react with other Filovirus members and as well as the human genome. Ten unique assays spanning the entire coding region were chosen for further evaluation. The human RPPH1 gene was chosen for the human positive control. The sequences of the primers and probes used are shown in Table 1.

```
Consensus sequence for the coding region
                                    SEQ ID NO: 37
ATGGATTCTCGTCCTCAGAAAGTCTGGATGACGCCGAGTCTCACTG

AATCTGACATGGATTACCACAAGATCTTGACAGCAGGTCTGTCCGT

TCAACAGGGGATTGTTCGGCAAAGAGTCATCCCAGTGTATCAAGTA

AACAATCTTGAGGAAATTTGCCAACTTATCATACAGGCCTTTGAAG

CTGGTGTTGATTTTCAAGAGAGTGCGGACAGTTTCCTTCTCATGCT

TTGTCTTCATCATGCGTACCAAGGAGATTACAAACTTTTCTTGGAA

AGTGGCGCAGTCAAGTATTTGGAAGGGCACGGGTTCCGTTTTGAAG

TCAAGAAGTGTGATGGAGTGAAGCGCCTTGAGGAATTGCTGCCAGC

AGTATCTAGTGGGAGAAACATTAAGAGAACACTTGCTGCCATGCCG

GAAGAGGAGACGACTGAAGCTAATGCCGGTCAGTTCCTCTCCTTTG

CAAGTCTATTCCTTCCGAAATTGGTAGTAGGAGAAAAGGCTTGCCT

TGAGAAGGTTCAAAGGCAAATTCAAGTACATGCAGAGCAAGGACTG

ATACAATATCCAACAGCTTGGCAATCAGTAGGACACATGATGGTGA

TTTTCCGTTTGATGCGAACAAATTTTTTGATCAAATTTCTTCTAAT

ACACCAAGGGATGCACATGGTTGCCGGACATGATGCCAACGATGCT

GTGATTTCAAATTCAGTGGCTCAAGCTCGTTTTTCAGGTCTATTGA

TTGTCAAAACAGTACTTGATCATATCCTACAAAAGACAGAACGAGG
```

-continued

AGTTCGTCTCCATCCTCTTGCAAGGACCGCCAAGGTAAAAAATGAG
GTGAACTCCTTCAAGGCTGCACTCAGCTCCCTGGCCAAGCATGGAG
AGTATGCTCCTTTCGCCCGACTTTTGAACCTTTCTGGAGTAAATAA
TCTTGAGCATGGTCTTTTCCCTCAACTGTCGGCAATTGCACTCGGA
GTCGCCACAGCCCACGGGAGCACCCTCGCAGGAGTAAATGTTGGAG
AACAGTATCAACAGCTCAGAGAGGCAGCCACTGAGGCTGAGAAGCA
ACTCCAACAATATGCGGAGTCTCGTGAACTTGACCATCTTGGACTT
GATGATCAGGAAAAGAAAATTCTTATGAACTTCCATCAGAAAAAGA
ACGAAATCAGCTTCCAGCAAACAAACGCGATGGTAACTCTAAGAAA
AGAGCGCCTGGCCAAGCTGACAGAAGCTATCACTGCTGCATCACTG
CCCAAAACAAGTGGACATTACGATGATGATGACGACATTCCCTTTC
CAGGACCCATCAATGATGACGACAATCCTGGCCATCAAGATGATGA
TCCGACTGACTCACAGGATACGACCATTCCCGATGTGGTAGTTGAC
CCCGATGATGGAGGCTACGGCGAATACCAAAGTTACTCGGAAAACG
GCATGAGTGCACCAGATGACTTGGTCCTATTCGATCTAGACGAGGA
CGACGAGGACACCAAGCCAGTGCCTAACAGATCGACCAAGGGTGGA

-continued

CAACAGAAAAACAGTCAAAAGGGCCAGCATACAGAGGGCAGACAGA
CACAATCCACGCCAACTCAAAACGTCACAGGCCCTCGCAGAACAAT
CCACCATGCCAGTGCTCCACTCACGGACAATGACAGAAGAAACGAA
CCCTCCGGCTCAACCAGCCCTCGCATGCTGACCCCAATCAACGAAG
AGGCAGACCCACTGGACGATGCCGACGACGAGACGTCTAGCCTTCC
GCCCTTAGAGTCAGATGATGAAGAACAGGACAGGGACGGAACTTCT
AACCGCACACCCACTGTCGCCCCACCGGCTCCCGTATACAGAGATC
ACTCCGAAAAGAAAGAACTCCCGCAAGATGAACAACAAGATCAGGA
CCACATTCAAGAGGCCAGGAACCAAGACAGTGACAACACCCAGCCA
GAACATTCTTTTGAGGAGATGTATCGCCACATTCTAAGATCACAGG
GGCCATTTGATGCCGTTTTGTATTATCATATGATGAAGGATGAGCC
TGTAGTTTTCAGTACCAGTGATGGTAAAGAGTACACGTATCCGGAC
TCCCTTGAAGAGGAATATCCACCATGGCTCACTGAAAAAGAGGCCA
TGAATGATGAGAATAGATTTGTTACACTGGATGGTCAACAATTTTA
TTGGCCAGTAATGAATCACAGGAATAAATTCATGGCAATCCTGCAA
CATCATCAGTGAA

TABLE 1

Primer and Probe Sequences

| AssaySet | SEQ ID NO: | Type | Sequence |
|---|---|---|---|
| ZE NP Assay Set 1 | SEQ ID NO: 01 | Forward | CATCATGCGTACCAAGGAGATTAC |
| ZE NP Assay Set 2 | SEQ ID NO: 02 | Forward | CCAGCAGTATCTAGTGGGAGAA |
| ZE NP Assay Set 3 | SEQ ID NO: 03 | Forward | CGCAGGAGTAAATGTTGGAGAA |
| ZE NP Assay Set 4 | SEQ ID NO: 04 | Forward | GGACAGGGACGGAACTTCTAA |
| ZE NP Assay Set 5 | SEQ ID NO: 05 | Forward | TGAAGCGCCTTGAGGAATTG |
| ZE NP Assay Set 6 | SEQ ID NO: 06 | Forward | GAAAGTGGCGCAGTCAAGTAT |
| ZE NP Assay Set 7 | SEQ ID NO: 07 | Forward | CACTCACGGACAATGACAGAAG |
| ZE NP Assay Set 8 | SEQ ID NO: 08 | Forward | TGATGAAGGATGAGCCTGTAGTT |
| ZE NP Assay Set 9 | SEQ ID NO: 09 | Forward | CATGCAGAGCAAGGACTGATAC |
| ZE NP Assay Set 10 | SEQ ID NO: 10 | Forward | CATGAGTGCACCAGATGACTTG |
| ZE NP Assay Set 1 | SEQ ID NO: 11 | Reverse | CGCTTCACTCCATCACACTTC |
| ZE NP Assay Set 2 | SEQ ID NO: 12 | Reverse | GACTTGCAAAGGAGAGGAACTG |
| ZE NP Assay Set 3 | SEQ ID NO: 13 | Reverse | GTTCACGAGACTCCGCATATTG |
| ZE NP Assay Set 4 | SEQ ID NO: 14 | Reverse | GTTCATCTTGCGGGAGTTCTTT |
| ZE NP Assay Set 5 | SEQ ID NO: 15 | Reverse | AGAGGAACTGACCGGCATTA |
| ZE NP Assay Set 6 | SEQ ID NO: 16 | Reverse | CATGGCAGCAAGTGTTCTCTTA |
| ZE NP Assay Set 7 | SEQ ID NO: 17 | Reverse | ATCTGACTCTAAGGGCGGAAG |
| ZE NP Assay Set 8 | SEQ ID NO: 18 | Reverse | TCAGTGAGCCATGGTGGATATT |
| ZE NP Assay Set 9 | SEQ ID NO: 19 | Reverse | CATGTGCATCCCTTGGTGTATT |
| ZE NP Assay Set 10 | SEQ ID NO: 20 | Reverse | TGTCTGTCTGCCCTCTGTATG |

TABLE 1-continued

Primer and Probe Sequences

| AssaySet | SEQ ID NO: | Type | Sequence |
|---|---|---|---|
| ZE NP Assay Set 1 | SEQ ID NO: 21 | Probe | TCAAGTATTTGGAAGGGCACGGGT |
| ZE NP Assay Set 2 | SEQ ID NO: 22 | Probe | ACCGGCATTAGCTTCAGTCGTCTC |
| ZE NP Assay Set 3 | SEQ ID NO: 23 | Probe | ACTGAGGCTGAGAAGCAACTCCAA |
| ZE NP Assay Set 4 | SEQ ID NO: 24 | Probe | ACCGGCTCCCGTATACAGAGATCA |
| ZE NP Assay Set 5 | SEQ ID NO: 25 | Probe | ATGCCGGAAGAGGAGACGACTGAA |
| ZE NP Assay Set 6 | SEQ ID NO: 26 | Probe | ATGGAGTGAAGCGCCTTGAGGAAT |
| ZE NP Assay Set 7 | SEQ ID NO: 27 | Probe | CCAATCAACGAAGAGGCAGACCCA |
| ZE NP Assay Set 8 | SEQ ID NO: 28 | Probe | AGTACACGTATCCGGACTCCCTTGAA |
| ZE NP Assay Set 9 | SEQ ID NO: 29 | Probe | ACAGCTTGGCAATCAGTAGGACACA |
| ZE NP Assay Set 10 | SEQ ID NO: 30 | Probe | ACACCAAGCCAGTGCCTAACAGAT |
| Hs RPPH1 | SEQ ID NO: 31 | Forward | GCGGAGGGAAGCTCATCAG |
| Hs RPPH1 | SEQ ID NO: 32 | Reverse | CCCTAGTCTCAGACCTTCCCAAG |
| Hs RPPH1 | SEQ ID NO: 33 | Probe | CACGAGCTGAGTGCGTCCTGTCAC |

The probes are labeled at the 5'-end with a FAM fluorophore, the 3'-end is labeled with an Iowa Black® FQ, and, reading 5' to 3', a ZEN quencher is positioned between bases 9 and 10.

Example 2

Validation of qPCR Assays

Ten different qPCR assays were validated using DNA PCR fragments (SEQ ID NO:34 and SEQ ID NO:35) (gBlocks, Integrated DNA Technologies) for the standard curve. The sequences include a T7 RNA polymerase promoter, and if transcribed, represent the negative strand of the Zaire Ebola virus NP gene. Each qPCR reaction contained 500 nM each Forward and Reverse primer (listed in Table 1), 250 nM FAM-ZEN labeled probe (listed in Table 1) (Integrated DNA Technologies), 3 mM MgCl$_2$, 0.8 mM dNTP mix, 0.4 U Immolase DNA polymerase (Bioline) in a final volume of 10 uL. Cycling conditions were $95^{10:00}$–$(95^{0:15}$–$60^{1:00})\times 40$ and the assays were run on a CFX384 real time thermocycler (BioRad). Zaire_Ebola_NP_frag1_negative strand_T7 (SEQ ID NO:34) was used as a standard curve for assays 1, 2, 3, 5, 6, 9. Zaire_Ebola_NP_frag2_negative strand_T7 (SEQ ID NO:35) was used as a standard curve for assays 4, 7, 8, 10. The standard curves ranged from 1E6-1E1 copies. A human specific target RPPH1 gene was also validated using a sense strand RPPH1 gBlock_T7 (Seq ID NO:36). The sequences of the gBlocks are shown in Table 2 (SEQ ID NO:34, SEQ ID NO:35 and SEQ ID NO:36), with the T7 promoter sequence underlined, and the start of transcription highlighted in uppercase bold. The PCR efficiency of each assay is given in Table 3, and was calculated using the instrument manufacturers supplied software. Each assay had a PCR efficiency of >90% and <105%.

TABLE 2 gBlock fragment sequence used to produce by IVT target RNA.

| Name | Sequence |
|---|---|
| SEQ ID NO: 34 Zaire_Ebola_NP_ frag1_negative strand_T7 | gaattc<u>taatacgactcactata</u>Gggagagt tcacgagactccgcatattgttggagttgct tctcagcctcagtggctgcctctctgagctg ttgatactgttctccaacatttactcctgcg agggtgctcccgtgggctgtggcgactccga gtgcaattgccgacagttgagggaaaagacc atgctcaagattatttactccagaaaggttc aaaagtcgggcgaaaggagcatactctccat gcttggccagggagctgagtgcagccttgaa ggagttcacctcattttttaccttggcggtc cttgcaagaggatggagacgaactcctcgtt ctgtcttttgtaggatatgatcaagtactgt tttgacaatcaatagacctgaaaaacgagct tgagccactgaatttgaaatcacagcatcgt tggcatcatgtccggcaaccatgtgcatccc ttggtgtattagaagaaatttgatcaaaaaa tttgttcgcatcaaacggaaaatcaccatca tgtgtcctactgattgccaagctgttggata ttgtatcagtccttgctctgcatgtacttga atttgcctttgaaccttctcaaggcaagcct tttctcctactaccaatttcggaaggaatag acttgcaaaggagaggaactgaccggcatta gcttcagtcgtctcctcttccggcatggcag caagtgttctcttaatgtttctcccactaga tactgctggcagcaattcctcaaggcgcttc actccatcacacttcttgacttcaaaacgga acccgtgcccttccaaatacttgactgcgcc acttccaagaaaagtttgtaatctccttgg tacgcatgatgaagacagcggccgc |
| SEQ ID NO: 35 Zaire_Ebola_NP_ frag2_negative strand_T7 | gaattc<u>taatacgactcactata</u>Gggagatt ctcatcattcatggcctcttttttcagtgagc catggtggatattcctcttcaagggagtccg gatacgtgtactctttaccatcactggtact gaaaactacaggctcatccttcatcatatga taatacaaaacggcatcaaatggcccctgtg atcttagaatgtggcgatacatctcctcaaa agaatgttctggctgggtgttgtcactgtct |

TABLE 2-continued gBlock fragment sequence used
to produce by IVT target RNA.

| Name | Sequence |
|---|---|
| | tggttcctggcctcttgaatgtggtcctgat<br>cttgttgttcatcttgcgggagttctttctt<br>ttcggagtgatctctgtatacgggagccggt<br>ggggcgacagtgggtgtgcggttagaagttc<br>cgtccctgtcctgttcttcatcatctgactc<br>taagggcggaaggctagacgtctcgtcgtcg<br>gcatcgtccagtgggtctgcctcttcgttga<br>ttggggtcagcatgcgagggctggttgagcc<br>ggagggttcgtttcttctgtcattgtccgtg<br>agtggagcactggcatggtggattgttctgc<br>gagggcctgtgacgttttgagttggcgtgga<br>ttgtgtctgtctgccctctgtatgctggccc<br>ttttgactgttttttctgttgtccacccttgg<br>tcgatctgttaggcactggcttggtgtcctc<br>gtcgtcctcgtctagatcgaataggaccaag<br>tcatctggtgcactcatgccgttttccgagt<br>aactttggtattcggcggccgc |
| SEQ ID NO: 36<br>RPPH1 gBlock_T7 | taatacgactcactataGggagaatagggcg<br>gagggaagctcatcagtggggccacgagctg<br>agtgcgtcctgtcactccactcccatgtccc<br>ttgggaaggtctgagactagggccagaggcg<br>gccctaacagggctctccctgagcttcgggg<br>aggtgagttcccagagaacggggctccgcgc<br>gaggtcagactgggcaggagatgccgtggac<br>ccgcccttcggggagggccggcggatgc<br>ctcctttgccggagcttggaacagactcacg<br>gccagcgaagtgagttcaatggctgaggtga<br>ggtaccccgcaggggacctcataacccaatt<br>cagactactctcctccgcccatt |

TABLE 3

PCR assay efficiencies calculated
from 6 log DNA standard curve.

| Assay | PCR efficiency |
|---|---|
| Set 1 | 92.9 |
| Set 2 | 92.6 |
| Set 3 | 93.1 |
| Set 4 | 90.5 |
| Set 5 | 92.4 |
| Set 6 | 95.8 |
| Set 7 | 92.3 |
| Set 8 | 92.5 |
| Set 9 | 94.1 |
| Set 10 | 94.8 |
| RPPH1 | 101.2 |

Example 3

Figure 1A:
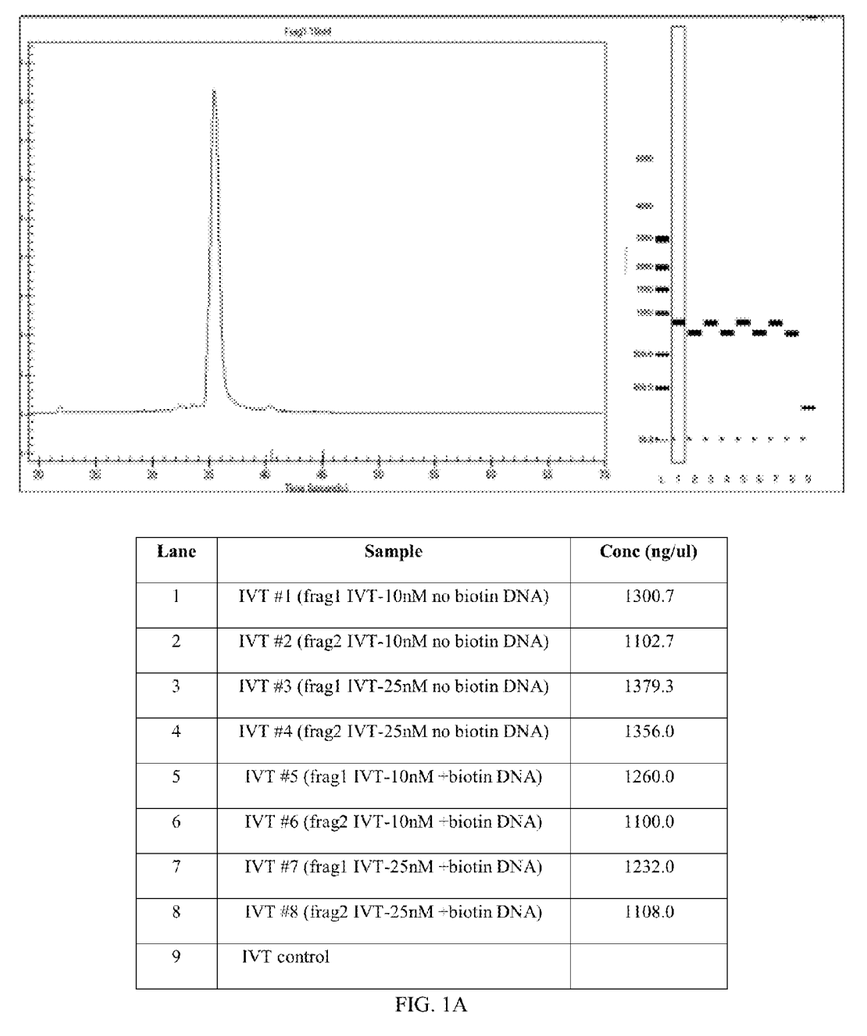
FIG. 1A is a graph of data generated from an electropherogram of the in vitro transcribed PCR products and lane descriptions.
Figure 1B:
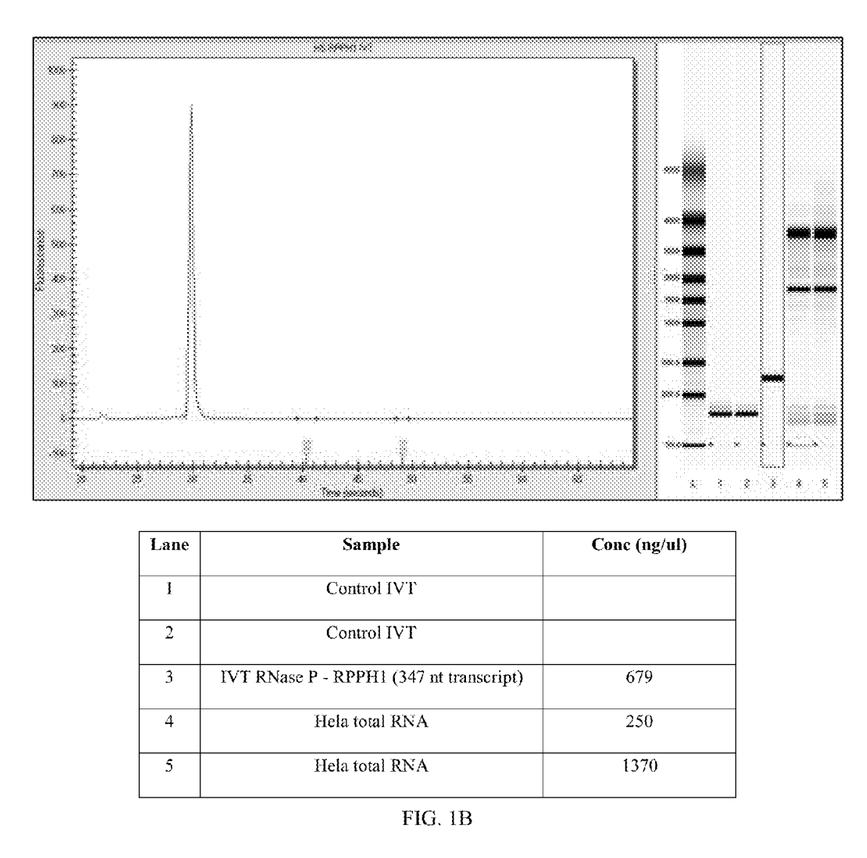
FIG. 1B is a graph of data generated from an electropherogram and lane descriptions.

Synthesis and Characterization of In Vitro Transcribed RNAs for Standards and Plasma Spike in Controls Negative strand RNA was generated from Zaire_Ebola_NP_frag1_negative strand_T7 gBlock (SEQ ID NO:34), using the MEGAshortscript T7 kit (Life Technologies) following the manufacturer recommended protocol using 10 nM final concentration of PCR product. The 870 base RNA was treated with TURBO DNase (Life Technologies) and purified using the MEGAclear kit (Life Technologies). The RNA was visualized on an Experion electrophoresis system (BioRad) as shown in FIG. 1A, Lane 1, and quantitated with a NanoDrop 2000 (Thermo Scientific). The RPPH1 RNA was generated in a similar manner using RRPH1 gBlock_T7 (SEQ ID NO:36) (25 nM final gBlock concentration). The 347 base RPPH1 RNA is shown in FIG. 1B, Lane 3. The electropherogram for each RNA shows a single major peak of the expected length.

Example 4

One Step RT-qPCR Quantification of Zaire Ebola Negative Strand NP Gene RNA

Figure 2A:
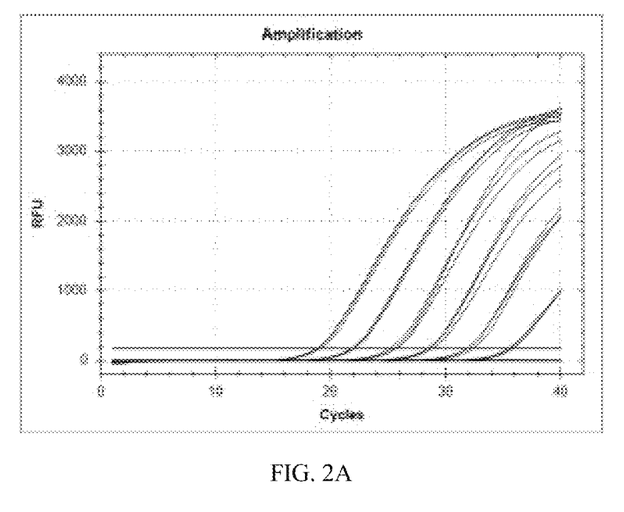
FIG. 2A is a graph of data from an Reverse Transcriptase RT-PCR from a sample of the in vitro transcribed product of RPPH1 gBlock_T7 (SEQ ID NO:37)
Figure 2B:
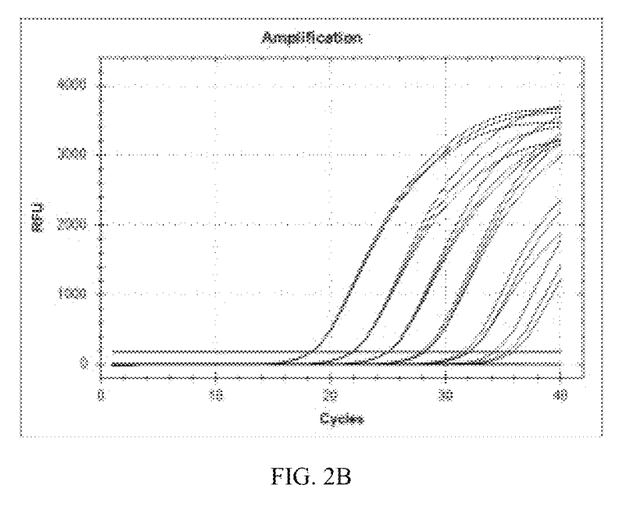
FIG. 2B is a graph of data generated form a Reverse Transcriptase RealTime-PCR from a sample of the in vitro transcribed product of Zaire_Ebola_NP_frag1_negative strand_T7 (SEQ ID NO:34) amplified with ZE NP Assay Set 3.

A standard curve (10 fold serial dilution) was generated using in vitro transcribed RNA from the Zaire_Ebola_NP_frag1_negative_strand_T7 gBlock (SEQ ID NO:34) and was used in a one-step RT-qPCR assay format to determine the assay efficiency for the combined reverse transcription and qPCR steps. Ten microliter reactions were set up using the SuperScript® III Platinum® One-Step qRT-PCR Kit (Life Technologies), 500 nM each forward and reverse primer (listed in Table 1), 250 nM FAM-ZEN quenched probe (listed in Table1)(Integrated DNA Technologies) and decreasing amounts of RNA from 1E6 to 1E1 copies, as well as a no template control. The Zaire_Ebola_NP_frag1_negative strand_T7 RNA (in vitro transcribed gBlock fragment SEQ ID NO:34) was in a background of 2.5 ng/uL HeLa cell total RNA to help mimic the complex nucleic acid background that would be present in extracted viral RNA from plasma. The RPPH1 RNA (in vitro transcribed from RPPH1 gBlock 17 gBlock fragment (SEQ ID NO:36)) was in a background of yeast tRNA at 100 ng/uL. FIG. 2A shows the standard curves for the RPPH1 one step RT-qPCR assay. The RPPH1 assay gave a calculated 99% PCR efficiency. FIG. 2B shows the standard curve for the Zaire Ebola NP Assay Set 3 one step RT-qPCR assay. The Zaire Ebola NP set 3 assay gave a calculated efficiency of 98.9%. Both assays showed no signal in the no template control wells. The limit of detection (LOD) for both assays was 10 copies.

Example 5

Detection of Zaire Ebola NP Gene RNA in Human Plasma

Figure 3A:
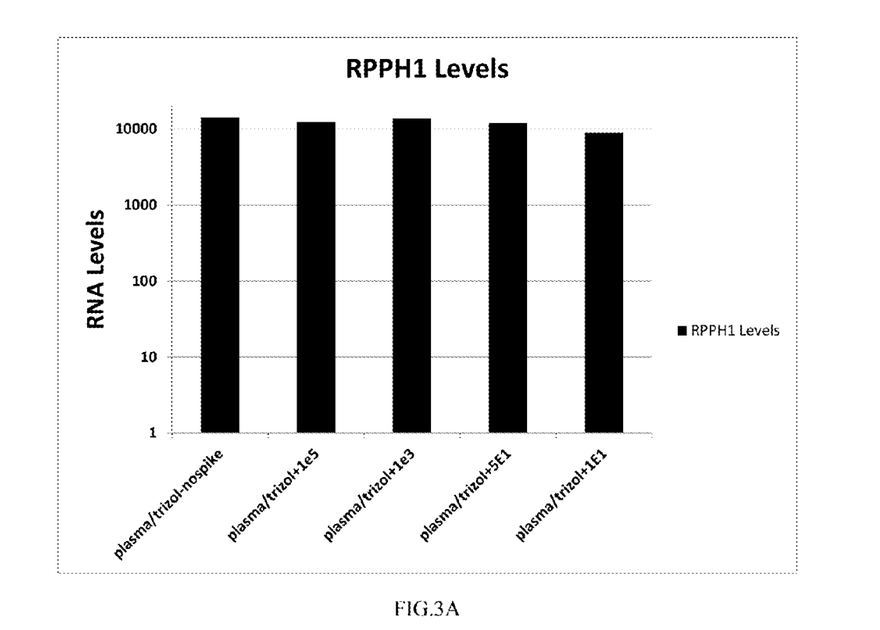
FIG. 3A is a graph of data showing the RPPH1 RNA levels for extracted samples.
Figure 3B:
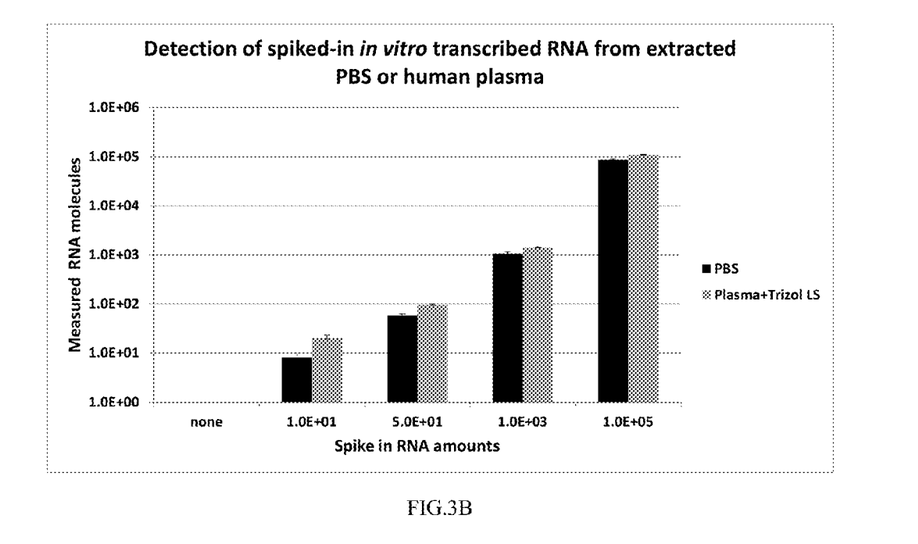
FIG. 3B is a graph of data showing the detection limit for spike in controls.

Human blood was collected in BD Vacutainer K2 EDTA Plasma Preparation Tubes (Becton, Dickinson and Company) and centrifuged at room temperature for 15 minutes at 2500 prm in an Allegra 6R centrifuge with a GH-3.8 swinging bucket rotor (Beckman Coulter). The plasma was removed and Trizol LS was added at 1 part plasma to 3 parts Trizol LS (Life Technologies) per manufacturer's recommendations and incubated at room temperature for 5 minutes. Nucleoprotein RNA (in vitro transcribed from Zaire_Ebola_NP_frag1_negative strand_T7; SEQ ID NO:34) was added into the plasma-Trizol LS mixture in amounts calculated to obtain an expected 1E1, 5E1, 1E3, and 1E5 molecules of RNA in the downstream RT-qPCR reaction. The RNA was extracted from the plasma-Trizol LS mixture using the QIAamp Viral RNA Mini Kit (Qiagen). RNA in 1×PBS was used for the mock extraction control. RNA was quantified using the SuperScript® III Platinum® One-Step qRT-PCR Kit as outlined in Example 4. The RPPH1 RNA levels for the various extracted samples vary by less than 1.7 fold and are shown in FIG. 3A. The normalized levels of Nucleoprotein RNA from extracted plasma samples compared to RNA in 1×PBS are indicated in FIG. 3B.

Isolating the nucleic acid sample per the QIAmp Viral RNA Mini Kit uses 140 uL of input sample (plasma-Trizol LS mixture or PBS), and final elution in 80 uL of buffer, of which 2 uL of the eluted material is added into the RT-qPCR reaction. The 10 copies of RNA detected in the RT-qPCR assay presented here correspond to an initial copy number of 1600 copies of NP RNA per 1 mL of plasma.

What is claimed is:

1. A method of determining the presence of a viral hemorrhagic fever virus nucleic acid in a sample comprising:
   a) contacting the sample with at least one probe selected from a group consisting of SEQ ID:21, SEQ ID NO:22, SEQ ID NO: 23, SEQ ID NO:24, SEQ ID NO:25, SEQ ID NO:26, SEQ ID NO: 27, SEQ ID NO:28, SEQ ID NO:29, or SEQ ID:30 capable of hybridizing under stringent conditions to the viral hemorrhagic fever nucleic acid; and detecting hybridization between the viral hemorrhagic fever nucleic acid and the probe, wherein the detection of hybridization indicates the presence of the viral hemorrhagic fever virus nucleic acid in the sample;
   wherein the viral hemorrhagic fever virus nucleic acid is an Ebola virus nucleic acid; and wherein the Ebola virus nucleic acid is SEQ ID NO: 37.

2. The method of claim 1, wherein the probe is labeled.

3. The method of claim 2, wherein the probe is radiolabeled, or fluorescently labeled.

4. The method of claim 2, wherein the probe is labeled with FAM and fluorescent quencher.

5. The method of claim 1, further comprising amplifying the viral hemorrhagic fever nucleic acid by polymerase chain reaction (PCR), reverse transcriptase polymerase PCR (RT-PCR), or real time reverse transcriptase PCR (rt RT-PCR).

6. The method of claim 5, wherein the amplifying employs primers that consist of the nucleotide sequences set forth as SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO: 13, SEQ ID NO:14, SEQ ID NO:15, SEQ ID NO:16, SEQ ID NO:17, SEQ ID NO: 18, SEQ ID NO: 19, or SEQ ID NO:20.

* * * * *